United States Patent
Watanabe et al.

(10) Patent No.: US 6,913,905 B1
(45) Date of Patent: Jul. 5, 2005

(54) REGULATORY SEQUENCES FUNCTIONING IN FILAMENTOUS FUNGI

(75) Inventors: Manabu Watanabe, Odawara (JP); Takeshi Murakami, Odawara (JP)

(73) Assignee: Meiji Seika Kaisha, Ltd., Tokyo-To (JP)

(*) Notice: Subject to any disclaimer, the term of this patent is extended or adjusted under 35 U.S.C. 154(b) by 283 days.

(21) Appl. No.: 10/070,386

(22) PCT Filed: Sep. 7, 2000

(86) PCT No.: PCT/JP00/06104

§ 371 (c)(1), (2), (4) Date: Mar. 6, 2002

(87) PCT Pub. No.: WO01/18219

PCT Pub. Date: Mar. 15, 2001

(30) Foreign Application Priority Data

Sep. 7, 1999 (JP) .......................................... 11-252851

(51) Int. Cl.⁷ ........................... C12P 21/02; C12N 1/00; C12N 1/15; C12N 5/10; C12N 15/11; C12N 15/63
(52) U.S. Cl. ................. 435/69.1; 435/243; 435/254.11; 435/320.1; 435/325; 435/419; 536/24.1
(58) Field of Search ...................... 536/24.1; 435/320.1, 435/243, 325, 419, 69.1, 254.11

(56) References Cited

FOREIGN PATENT DOCUMENTS

| EP | 0 382 173 | 8/1990 |
| EP | 0 780 468 | 6/1997 |
| JP | 7-123987 | 5/1995 |
| JP | 11-276170 | 10/1999 |

*Primary Examiner*—Terry McKelvey
(74) *Attorney, Agent, or Firm*—Wenderoth, Lind & Ponack L.L.P.

(57) ABSTRACT

The present invention provides a promoter and a terminator which coordinately function with the expression of an endogenous gene in a filamentous fungus that belongs to *Agonomycetes*, particularly in *Mycelia sterilia*. A promoter of the present invention comprises the nucleotide sequence of SEQ ID NO: 1 and a homologue thereof. A terminator of the present invention comprises the nucleotide sequence of SEQ ID NO: 2 and a homologue thereof. The present invention further provides an expression vector that highly expresses a protein of interest in a filamentous fungus, a transformed filamentous fungus that highly produces a protein of interest, and a process of producing the protein of interest in the transformed filamentous fungus.

14 Claims, 1 Drawing Sheet

REGULATORY SEQUENCES FUNCTIONING IN FILAMENTOUS FUNGI

This application is a 371 of PCT/JP00/06104 filed Sep. 7, 2000.

BACKGROUND OF THE INVENTION

1. Field of the Invention

The present invention relates to promoters and terminators which function in filamentous fungi, expression vectors comprising the same, and hosts transformed by said vectors.

2. Description of the Related Art

The filamentous fungus strain PF1022 (*Mycelia sterilia*) (FERM BP-2671) produces substance PF1022 which is a 24-membered cyclic depsipeptide having a vermifugal activity. This strain has been classified into *Agonomycetes* since it forms no sexual or asexual organ (Japanese Patent Application Laid-open No. 35796/1991).

On the other hand, a transformant of the strain PF1022 has been obtained by introducing a plasmid in which the TAKA-amylase gene derived from *Aspergillus oryzae* is ligated along with a drug resistance gene into the strain PF1022 (WO97/00944).

However, the regulatory DNA sequence of the TAKA-amylase gene derived from *Aspergillus oryzae* reported in WO97/00944 is a regulatory DNA sequence derived from a strain of heterologous species. Moreover, genetic characteristics of *Mycelia sterilia* have not sufficiently been revealed and the condition to satisfy expression vector systems has not been elucidated. Accordingly, it is not clear whether gene expression in a transformant having a regulatory sequence derived from a strain of heterologous species can be coordinately regulated with the expression of an endogenous gene in the strain PF1022. Furthermore, since the strain PF1022 belongs to *Agonomycetes*, it is also not clear whether conventional regulatory DNA sequences used in microorganisms other than genus *Aspergillus*, such as genus *Trichoderma*, genus *Fusarium*, genus *Neurospora* or the like, can be appropriately expressed.

Accordingly, a regulatory sequence and an expression vector system which stably function in *Mycelia sterilia*, and establishment of technology for producing useful substances in *Mycelia sterilia* using the same are highly desired.

SUMMARY OF THE INVENTION

An objective of the present invention is to provide a regulatory sequence that functionally coordinates with the expression of an endogenous gene in a filamentous fungus that belongs to *Agonomycetes*, particularly in *Mycelia sterilia*.

Another objective of the present invention is to provide an expression vector that highly expresses a protein of interest in a filamentous fungus that belongs to *Agonomycetes*, particularly in *Mycelia sterilia*.

Still another objective of the present invention is to provide a process of producing a protein of interest in a filamentous fungus that belongs to *Agonomycetes*, particularly in *Mycelia sterilia*.

The present inventors succeeded in isolating and identifying a highly expressing gene (Abp1 gene) and its regulatory DNA sequences.

The present inventors also succeeded in constructing an expression vector for gene expression using the regulatory DNA sequences thus obtained, introducing this vector into a PF1022-producing microorganism to obtain a transformant, and highly expressing a gene of interest ligated downstream of the promoter of this transformant without making the gene malfunction.

A promoter according to the present invention comprises a nucleotide sequence selected from the group consisting of the following sequences, and a fragment thereof having promoter activity:

(a) a nucleotide sequence of SEQ ID NO: 1,
(b) a nucleotide sequence that has at least 70% homology to the sequence of SEQ ID NO: 1 and has promoter activity,
(c) a modified nucleotide sequence of SEQ ID NO: 1 that has one or more modifications selected from a substitution, a deletion, an addition and an insertion and has promoter activity, and
(d) a nucleotide sequence that hybridizes with a nucleotide sequence of SEQ ID NO: 1 under stringent conditions and has promoter activity.

A terminator according to the present invention comprises a nucleotide sequence selected from the group consisting of the following sequences, and a fragment thereof having terminator activity:

(e) a nucleotide sequence of SEQ ID NO: 2,
(f) a nucleotide sequence that has at least 70% homology to the nucleotide sequence of SEQ ID NO: 2 and has terminator activity,
(g) a modified nucleotide sequence of SEQ ID NO: 2 that has one or more modifications selected from a substitution, a deletion, an addition and an insertion and having terminator activity, and
(h) a nucleotide sequence that hybridizes with a nucleotide sequence of SEQ ID NO: 2 under stringent conditions and has terminator activity.

An expression vector of the present invention comprises either one or both of the abovementioned promoter or a fragment thereof and the above-mentioned terminator or a fragment thereof.

A transformed host according to the present invention is a host transformed with the abovementioned expression vector.

A process for producing a substance of interest according to the present invention comprises culturing the above-mentioned transformed host and collecting the protein of interest from the culture medium.

DETAILED DESCRIPTION OF THE INVENTION

Deposition of Microorganism

Figure 1:
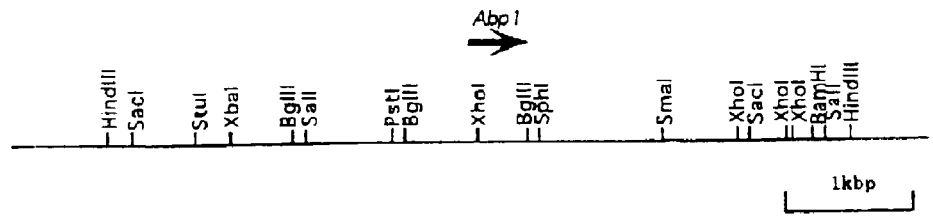
FIG. 1 shows a restriction map of a 6 kb HindIII fragment comprising the Abp1 gene.

The strain PF1022 was deposited with the National Institute of Bioscience and Human-Technology Agency of Industrial Science and Technology, the Ministry of International Trade and Industry (1-3 Higashi 1-Chome, Tsukuba City, Ibaraki Prefecture, Japan), dated Jan. 24, 1989. The accession number is FERM BP-2671.

Regulatory Sequences

According to the present invention, there are provided regulatory sequences, namely a promoter and a terminator, which function in a PF1022-producing microorganism.

Sequence (b) can have preferably at least 80%, more preferably at least 90%, or most preferably at least 95% homology to the nucleotide sequence of SEQ ID NO: 1.

Sequence (f) can have preferably at least 80%, more preferably at least 90%, or most preferably at least 95% homology to the nucleotide sequence of SEQ ID NO: 2.

In sequences (c) and (g), the number of modifications can be, for example, one to dozens.

In sequences (c) and (g), if multiple modifications are introduced, said modifications may be the same or different.

In sequences (d) and (h), the term "stringent conditions" means that a membrane after hybridization is washed at a high temperature in a solution of low salt concentration, for example, at 60° C. for 15 minutes in a solution of 0.5×SSC concentration (1×SSC: 15 mM trisodium citrate, 150 mM sodium chloride), more preferably at 60° C. for 15 minutes in solution of 0.5×SSC concentration and 0.1% SDS.

The length of a fragment having promoter activity can be at least 600 base pairs, preferably at least 800 base pairs, more preferably at least 1000 base pairs, and most preferably at least 1200 base pairs.

The length of a fragment having terminator activity can be at least 400 base pairs, preferably at least 600 base pairs, more preferably at least 800 base pairs, and most preferably at least 1000 base pairs.

Whether sequences (b), (c) and (d) and fragments having promoter activity "have the promoter activity" or not can be evaluated, for example, by constructing an expression vector as described in Example 3, expressing a heterologous gene in a host as described in Example 4, and detecting the production of a heterologous protein.

Whether sequences (f), (g) and (h) and fragments having terminator activity "have the terminator activity" or not can be evaluated, for example, by constructing an expression vector as described in Example 3, expressing a heterologous gene in a host as described in Example 4, and detecting the production of a heterologous protein.

A promoter and a terminator according to the present invention can function in a filamentous fungus that is classified into *Agonomycetes*, particularly a microorganism that belongs to *Mycelia*, more specifically a microorganism that belongs to *Mycelia sterilia*.

A promoter and a terminator according to the present invention can function in a PF1022-producing microorganism. An example of the PF1022-producing microorganism is a filamentous fungus that is classified into *Agonomycetes* producing the substance PF1022.

A promoter and a terminator according to the present invention can be obtained, for example, as follows.

mRNAs of the strain PF1022 are isolated from the cells during substance PF1022 production and cDNAs are synthesized using the isolated mRNAs as a template. The cDNAs are randomly sampled and the DNA sequences of the sampled cDNAs are analyzed to isolate cDNAs derived from a highly expressing gene, namely the Abp1 gene.

A genomic DNA is isolated from the strain PF1022 and cleaved with appropriate restriction enzymes, and a library comprising the genomic DNA of the PF1022-producing microorganism is constructed using a phage vector or a plasmid vector.

The entire length of the Abp1 gene is cloned from the genomic DNA library derived from the strain PF1022 thus prepared using a translation region encoding the Abp1 gene as a probe. The isolated genomic DNA and the DNA sequence of the above-mentioned cDNAs are compared and promoter and terminator sites of this gene are determined to identify a promoter and a terminator.

Expression Vectors

The present invention provides an expression vector comprising a regulatory sequence which functions in a PF1022-producing microorganism.

The procedure and method for constructing an expression vector according to the present invention can be any of those commonly used in the field of genetic engineering.

Examples of the expression vector as used herein include vectors which can be incorporated into a host chromosome DNA and vectors having a self-replicable autonomous replication sequence which can be present as a plasmid in a host cell, for example, pUC vectors (e.g., pUC18 and pUC118), pBluescript vectors (e.g., pBluescriptII KS+), and plasmids such as pBR322 plasmid. One or more of copies of the gene can be present in a host cell.

An expression vector according to the present invention in the first embodiment comprises a promoter and/or a terminator according to the present invention, and if appropriate, a gene marker and/or other regulatory sequences. Thus, an expression vector comprising either one or both of the promoter and the terminator according to the present invention is within the scope of the present invention.

An expression vector that at least comprises the promoter according to the present invention can comprise a terminator other than the terminator according to the present invention.

An expression vector that at least comprises the terminator according to the present invention can comprise a promoter other than the promoter according to the present invention.

A gene marker can be introduced, for example, by introducing an appropriate restriction enzyme cleaving site into a regulatory sequence of the present invention by the PCR method, inserting this into a plasmid vector, and ligating a selective marker gene such as a drug resistance gene and/or a gene complementing a nutritional requirement.

A gene marker can be appropriately selected depending on the technique for selecting a transformant. For example, a gene encoding drug resistance or a gene complementing a nutritional requirement can be used. Examples of the drug resistance gene include genes conferring resistance to destomycin, benomyl, oligomycin, hygromycin, G418, bleomycin, bialaphos, blastcidin S, phleomycin, phosphinothricin, ampicillin, and kanamycin. Examples of the gene complementing a nutritional requirement include amdS, pyrG, argB, trpC, niaD, TRP1, LEU2, URA3 and the like.

An expression vector according to the present invention in the second embodiment can further comprise a nucleotide sequence encoding a protein of interest, which is operably linked to a regulatory sequence.

The ligation to a regulatory sequence can be carried out, for example, according to an ordinary method by inserting a translation region of a gene encoding a protein of interest (gene of interest) downstream of a promoter in the right direction. In this case, the protein can be expressed as a fusion protein by ligating the gene of interest with a foreign gene encoding a translation region of another protein. In the present specification, the term "gene of interest" means a given gene to be subjected to expression and can be either a heterologous gene or a homologous gene. The gene of interest can be, for example, a gene selected from a group related to the production of substance PF1022.

Production of Transformant and Protein of Interest

The present invention provides a host transformed with the above-mentioned expression vector. A host to be used in the present invention is not particularly restricted and any microorganism which can be used as a host for genetic recombination, for example, a filamentous fungus, preferably a filamentous fungus classified into *Agonomycetes*, more preferably a microorganism that belongs to *Mycelia*, most preferably a microorganism that belongs to *Mycelia sterilia*, can be used. Examples of the host to be used in the present invention include a PF1022-producing microorganism, preferably a filamentous fungus producing substance PF1022, more preferably the strain PF1022 (FERM BP-2671) producing substance PF1022.

A recombinant vector for the gene expression can be introduced into a host by an ordinary method. Examples of the method for the introduction include the electroporation method, the polyethylene glycol method, the aglobacterium method, the lithium method, and the calcium chloride method. A method suitable to each host cell can be selected. The polyethylene glycol method is preferable when a PF1022-producing microorganism is used as a host.

The present invention provides a process for producing a protein of interest including a step of culturing the above-mentioned transformant.

A transformant can be cultured according to an ordinary method by using a medium, culture conditions and the like, which are appropriately selected. Conventional components can be used for a medium. As a carbon source, glucose, sucrose, cellulose, starch syrup, dextrin, starch, glycerol, molasses, animal and vegetable oils, and the like can be used. As a nitrogen source, soybean powder, wheat germ, pharma media, cornsteep liquor, cotton seed lees, bouillon, peptone, polypeptone, malt extract, ammonium sulfate, sodium nitrate, urea, and the like can be used. If necessary, sodium, potassium, calcium, magnesium, cobalt, chlorine, phosphoric acid, sulfuric acid, and other inorganic salts that can produce ions, such as potassium chloride, calcium carbonate, dipotassium hydrogenphosphate, magnesium sulfate, monopotassium phosphate, zinc sulfate, manganese sulfate, and copper sulfate, can be effectively added. If necessary, various vitamins such as thiamine (e.g., thiamine hydrochloride), amino acids such as glutamic acid (e.g., sodium glutamate) and asparagine (e.g., DL-asparagine), trace nutrients such as nucleotides, and selective drugs such as antibiotics can be added. Further, organic and inorganic substances to promote the growth of microorganisms and enhance the production of cyclic depsipeptide can be appropriately added.

The cultivation can be carried out in a liquid medium by a culture method under an aerobic condition, a shaking culture method, an agitation culture method with aeration, or a submerged culture method. The pH of the medium is, for example, about 6 to 8. The cultivation can be carried out at a normal temperature, such as 14° C. to 40° C., preferably 26° C. to 37° C., for about 2 to 25 days.

Furthermore, in a process of producing a protein of interest according to the present invention, the protein of interest, namely the gene expression product, can be obtained from the culture of transformed cells. The protein of interest can be extracted from the culture (e.g., by mashing, and crushing under pressure), recovered (e.g., by filtration, and centrifugation), and purified (e.g., by salting out, and solvent precipitation). Furthermore, in these steps, a protease inhibitor such as phenylmethylsulfonyl fluoride (PMSF), benzamidine and leupeptin can be added, if necessary.

EXAMPLE

The present invention is further illustrated by the following examples that are not intended as a limitation of the invention.

Example 1

Search for a Highly Expressing Gene by Random Sequencing of cDNA

In order to search for a highly expressing gene in a substance PF1022-producing microorganism, cDNAs derived from the substance PF1022-producing microorganism were randomly cloned, DNA sequences of the products were compared, and a gene which was highly expressed was isolated and identified.

(1) Preparation of cDNA Derived from a Substance PF1022-producing Microorganism

The strain PF1022 (FERM BP-2671) was cultured in a production medium (2.0% glucose, 5.0% starch, 0.8% wheat germ, 1.3% soybean cake, 0.38% meat extract, 0.13% sodium chloride, and 0.15% calcium carbonate; pH 7.0 before sterilization; see Example 4 in WO97/00944) at 26° C. for 4 days, and the resulting cells were recovered by centrifugation (3000 rpm, 10 minutes). The cells were washed with purified water, frozen at −80° C., and then smashed with a blender (AM-3, Nippon Seiki Industry Co., Ltd.) under the presence of liquid nitrogen. The resulting smashed cells were suspended in a denaturation solution (4 M guanidine thiocyanate, 25 mM trisodium citrate, 0.5% sodium N-lauryl sarcosinate, 0.1M mercapto ethanol), the suspension was stirred at room temperature for 5 minutes and then neutralized with 2 M sodium citrate (pH 4.5), TE-saturated phenol was added, and the resulting admixture was further stirred. Chloroform-isoamyl alcohol (24:1) was added to the admixture and after stirring, the cell component denatured with phenol was isolated by centrifugation. The upper layer (aqueous layer) was recovered, and the nucleic acid was precipitated with isopropanol. The precipitate was dissolved in a TE solution (10 mM tris-hydrochloric acid (pH 8.0), 1 mM EDTA) to a nucleic acid concentration of 1 mg/ml and then precipitated with 2.5 M lithium chloride (5° C., 2 hours). The resulting precipitate was recovered by centrifugation, washed with 70% ethanol and redissolved in a TE solution to obtain the total RNA fraction.

From this total RNA fraction, mRNA was purified using an mRNA purification kit (Amersham Pharmadia Biotech).

Further, cDNA was synthesized using this mRNA as a template using a Timesaver cDNA synthesis kit (Amersham Pharmacia Biotech).

(2) Random Sequencing of cDNA

The cDNA prepared in Example 1 (1) was cleaved with EcoRI, after which ligation to pUC18 treated with alkaline phosphatase was carried out using a DNA ligation kit Ver. 2 (Takara Shuzo Co., Ltd.). Transformation was carried out with E. coli JM109 strain and various transformed colonies were cultured in an LB medium (1% polypeptone, 0.5% yeast extract, 1% sodium chloride) supplemented with ampicillin. Plasmids from these transformants were purified using a Flexi Prep kit (Amersham Pharmacia Biotech).

Forty kinds of plasmids prepared as described above were subjected to an ALF DNA sequencer II (Amersham Pharmacia Biotech) and the DNA sequences of inserted fragments were analyzed. The sequence gel used was Long Ranger (FMC Co.) and the sequencing reaction was carried out using an Autoread sequencing kit (Amersham Pharmacia Biotech).

As a result, ten kinds of clones were found to have an identical DNA sequence. The cloned gene was named Abp1, and the promoter and the terminator of this gene were to be cloned from the genomic DNA.

(3) Isolation of Genomic DNA of Substance PF1022-producing Microorganism

The genomic DNA of the strain PF1022 was isolated according to the method of Horiuchi et al. (H. Horiuchi et al., J. Bacteriol., 170, 272–278, 1988). More specifically, cells of substance PF1022-producing strain (FERM BP-2671) were cultured for 2 days in a seed medium (2.0% soluble starch, 1.0% glucose, 0.5% polypeptone, 0.6% wheat germ, 0.3% yeast extract, 0.2% soybean cake, and 0.2% calcium carbonate; pH 7.0 before sterilization; see Example 1 in WO97/00944) and the cells were recovered by centrifugation (3500 rpm, 10 minutes). The cells thus obtained were lyophilized and then suspended in a TE solution, treated in a 3% SDS solution at 60° C. for 30 minutes, and then subjected to TE-saturated phenol extraction to remove the cell residue. The extract was precipitated with ethanol and treated with ribonuclease A (Sigma) and proteinase K (Wako Pure Chemical Industries, Ltd.), and then the nucleic acid was precipitated with 12% polyethylene glycol 6000. The precipitate was subjected to TE-saturated phenol extraction and ethanol precipitation, and the resulting precipitate was dissolved in a TE solution to obtain the genomic DNA.

(4) Construction of Genomic DNA Library of Substance PF1022-producing Microorganism The genomic DNA derived from the substance PF1022-producing microorganism prepared in Example 1 (3) was partially digested with Sau3AI. The product was ligated to the BamHI arm of a phage vector, λEMBL3 cloning kit (Stratagene Co.) using T4 ligase (Ligation Kit ver. 2; Takara Shuzo Co., Ltd.). After ethanol precipitation, the precipitate was dissolved in a TE solution. The entire ligated mixture was used to infect E. coli LE392 strain using a Gigapack II Plus Packaging kit (Stratagene Co.) to form a phage plaque. The $1.3 \times 10^4$ ($2.6 \times 10^4$ PFU/ml) phage library obtained by this method was used for cloning of the Abp1 gene.

(5) Cloning of the Abp1 Gene from the Genomic DNA Derived from Substance PF1022-producing Microorganism A probe to be used was prepared by amplifying the translation region of the Abp1 gene by the PCR method. The PCR was carried out using the genomic DNA prepared in Example 1 (3) as a template and synthesis primers 8-73U and 8-73R according to a LETS GO PCR kit (SAWADY Technology). The PCR reaction for amplification was conducted by repeating 25 cycles of 30 seconds at 94° C., 30 seconds at 50° C., and 90 seconds at 72° C. DNA sequences of the 8-73U and 8-73R are as follows:

8-73U: CACAAACCAGGAACTCTTTC (SEQ ID NO: 7)
8-73R: GACATGTGGAAACCACATTTTG (SEQ ID NO: 8)

The PCR product thus obtained was labeled using an ECL Direct System (Amersham Pharmacia Biotech). The phage plaque prepared in Example 1 (4) was transferred to a Hibond N+ nylon transfer membrane (Amersham Pharmacia Biotech), and after alkaline denaturation, the membrane was washed with 5-fold concentration SSC (SSC: 15 mM trisodium citrate, 150 mM sodium chloride), and dried to immobilize the DNA. According to the kit protocol, prehybridization (42° C.) was carried out for 1 hour, after which the previously labeled probe was added and hybridization was carried out at 42° C. for 16 hours. The probe was washed according to the kit protocol above. The nylon membrane used with the washed probe was immersed for one minute in a detection solution, and was then photosensitized on a medical X-ray film (Fuji Photo Film Co., Ltd.) to obtain one positive clone. Southern blot analysis of this clone showed that a HindIII fragment of at least 6 kb was identical with the restriction enzyme fragment of the genomic DNA. FIG. 1 shows the restriction map of this HindIII fragment. The HindIII fragment was subcloned in pUC119 to obtain pRQHin/119 for the following experiment.

Example 2

Determination of DNA Sequences of Promoter and Terminator of Abp1 Gene

A template for DNA sequence analysis was prepared by digesting pRQHin/119 with SalI and SmaI and ligating the resultant fragment with pUC18 previously digested with the same restriction enzymes. The DNA sequence analysis was carried out in the same manner as described in Example 1 (2). Next, the DNA sequence thus obtained was compared with that of cDNA obtained in Example 1 (2), and sequences of the promoter and terminator regions of the Abp1 gene were determined. The resulting DNA sequences are shown in SEQ ID NO: 1 and SEQ ID NO: 2.

Example 3

Construction of Expression Vector Using the Expression Regulatory Region of the Abp1 Gene The promoter region and the terminator region of the Abp1 gene were amplified by the PCR method using pRQHin/119 as a template. The PCR method was carried out using PCR Super Mix High Fidelity (Lifetech Oriental Co., Ltd.) with primers ABP-Neco and ABP-Nbam for promoter amplification and ABP-Cbam and ABP-Cxba for terminator amplification. The amplification reaction was conducted by repeating 25 cycles of 30 seconds at 94° C., 30 seconds at 50° C. and 90 seconds at 72° C. The DNA sequences of ABP-Neco, ABP-Nbam, ABP-Cbam and ABP-Cxba are as follows:

ABP-Neco: GGGGAATTCGTGGGTGGTGATAT-
CATGGC (SEQ ID NO: 3)
ABP-Nbam: GGGGGATCCTTGATGGGTTTTGGG (SEQ
ID NO: 4)
ABP-Cbam: GGGGGATCCTAAACTCCCATCTATAGC
(SEQ ID NO: 5)
ABP-Cxba: GGGTCTAGACGACTCATTGCAGT-
GAGTGG (SEQ ID NO: 6)

Figure 2:
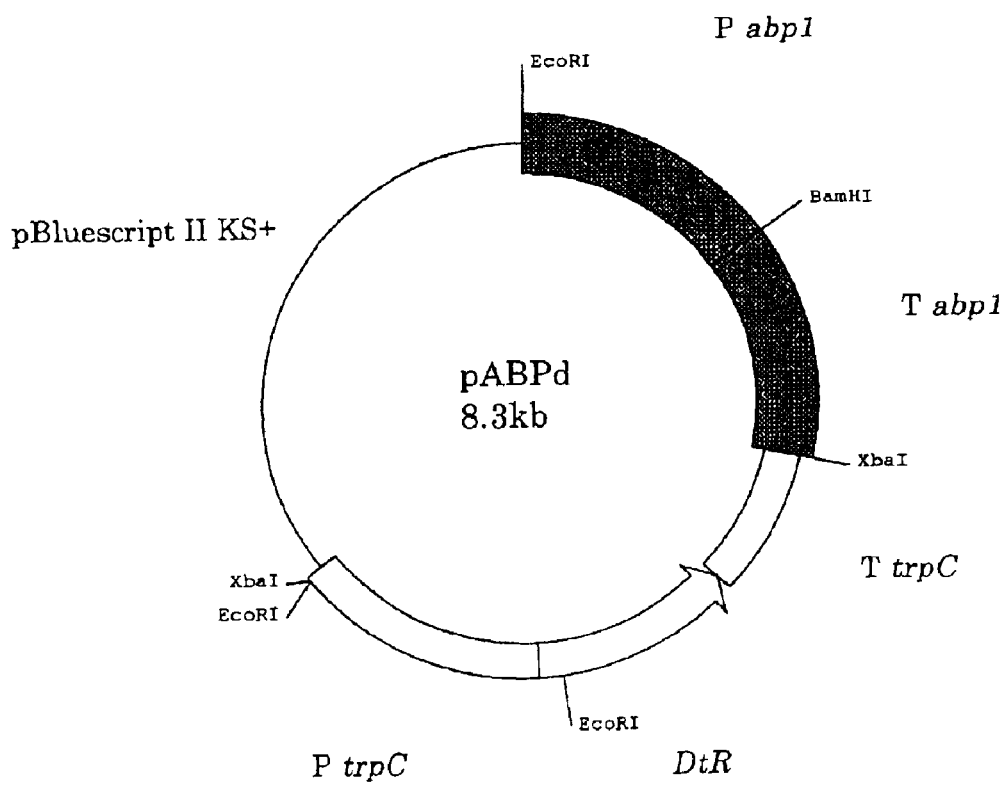
FIG. 2 shows the construction and restriction map for pABPd.

Each PCR product was purified with a Microspin S-400 column (Amersham Pharmacia Biotech) and precipitated with ethanol, after which the promoter was digested with EcoRI and BamI, the terminator was digested with BamHI and XbaI, and the resulting fragments were ligated one by one with pBleuscriptII KS+ previously digested with the same enzymes. The product was digested with XbaI, and a destomycin resistance cassette derived from pMKD01 (WO98/03667) was inserted to construct pABPd (FIG. 2).

Example 4
Confirmation of Ability of Expression Vector Using β-glucuronidase Gene The translation region of the β-glucuronidase (GUS) gene used as a reporter gene was obtained by digesting pLC-GUS (K. Yanai, et al., Biosci. Biotech. Biochem., 60, 472–475, 1996) with BamHI. This fragment was ligated with pABPd which was previously digested with BamHI and treated with alkaline phosphatase to construct plasmid pABPd-G in which the GUS gene was inserted downstream of the Abp1 promoter.

The microorganism producing substance PF1022 (FERM BP-2671) was transformed with pABPd-G according to the method described in Example 1 of WO97/00944. As a result, about three transformants per 1 μg of DNA were obtained.

The transformants thus obtained were cultured in a liquid using the production medium of Example 1 (1) and the cells were recovered by centrifugation. The resultant cells were disrupted using a Mini-Bead beater (Biospeck Products). Cell debris was removed by centrifugation and the supernatant was measured for GUS activity. The activity was measured by the method described in K. Yanai, et al., Biosci. Biotech. Biochem., 60, 472–475, 1996.

Results in Table 1 evidently confirmed that only the pABPd-G transformants had marked GUS activity. Namely, it was confirmed that the expression vector pABPd effectively functions in the substance PF1022-producing microorganism.

TABLE 1

GUS Activity of Transformants

|  | Expression vector | GUS activity (A405/μg protein) |
|---|---|---|
| Transformant | pABPd-G | 756.9 |
| Transformant | pABPd-G | 832.5 |
| Transformant | pABPd | 0.0 |
| Host | — | 0.0 |

What is claimed is:

1. An isolated promoter comprising a nucleotide sequence or a fragment thereof having promoter activity, which nucleotide sequence is selected from the group consisting of the following sequences:
   (a) the nucleotide sequence of SEQ ID NO: 1,
   (b) a nucleotide sequence that has at least 95% homology to the sequence of SEQ ID NO: 1 and has promoter activity, and
   (c) a nucleotide sequence that hybridizes with the nucleotide sequence of SEQ ID NO: 1 under stringent conditions and has promoter activity, wherein the stringent conditions comprise a wash at 60° C. for 15 minutes in a solution of 0.5×SSC concentration and 0.1% SDS.

2. The isolated promoter according to claim 1, which functions in a filamentous fungus that belongs to *Agonomycetes*.

3. The isolated promoter according to claim 1, wherein the length of the fragment having promoter activity is at least 600 bp.

4. An isolated expression vector comprising the promoter or the fragment thereof according to claim 1.

5. An isolated expression vector comprising a promoter comprising a nucleotide sequence or a fragment thereof having promoter activity, which nucleotide sequence is selected from the group consisting of the following sequences:
  (a) the nucleotide sequence of SEQ ID NO: 1,
  (b) a nucleotide sequence that has at least 95% homology to the sequence of SEQ ID NO: 1 and has promoter activity, and
  (c) a nucleotide sequence that hybridizes with the nucleotide sequence of SEQ ID NO: 1 under stringent conditions and has promoter activity, wherein the stringent conditions comprise a wash at 60° C. for 15 minutes in a solution of 0.5×SSC concentration and 0.1% SDS, together with a terminator comprising a nucleotide sequence or a fragment thereof having terminator activity, which nucleotide sequence is selected from the group consisting of the following sequences:
  (i) the nucleotide sequence of SEQ ID NO: 2,
  (ii) a nucleotide sequence that has at least 95% homology to the nucleotide sequence of SEQ ID NO: 2 and has terminator activity, and
  (iii) a nucleotide sequence that hybridizes with the nucleotide sequence of SEQ ID NO: 2 under stringent conditions and has terminator activity, wherein the stringent conditions comprise a wash at 60° C. for 15 minutes in a solution of 0.5×SSC concentration and 0.1% SDS.

6. The isolated expression vector according to claim 5, wherein the expression vector is pABPd.

7. The isolated expression vector according to claim 4, which further comprises a nucleotide sequence encoding a protein of interest, wherein the nucleotide sequence is operably linked to the promoter and/or the terminator.

8. A host cell transformed with the expression vector of claim 7.

9. The host cell according to claim 8, wherein the host cell is *Mycelia sterilia*.

10. A method for producing a protein of interest, which comprises culturing the host cell of claim 8 and collecting the protein of interest from the culture medium.

11. The expression vector according to claim 5, which further comprises a nucleotide sequence encoding a protein of interest, wherein the nucleotide sequence is operably linked to the promoter and/or the terminator.

12. A host cell transformed with the expression vector of claim 11.

13. The host cell according to claim 12, wherein the host cell is *Mycelia sterilia*.

14. A method for producing a protein of interest, which comprises culturing the host cell of claim 12 and collecting the protein of interest from the culture medium.

* * * * *

SEQUENCE LISTING

<160> NUMBER OF SEQ ID NOS: 8

<210> SEQ ID NO 1
<211> LENGTH: 1378
<212> TYPE: DNA
<213> ORGANISM: Mycelia sterilia

<400> SEQUENCE: 1

```
gtcgacgtgg gtggtgatat catggctgtg gtgtccaaaa ctgtgttagt gactacgaat      60
gaggaaagaa acggtggtgt tgtggcagct gaagactgaa gaaggagcca aagataattc     120
acaatgcgat acgttgcat caatgcttgt tcaagagagc acgttgcatc tacctggtgt     180
tcccctcttc gttgtacaag atcaagtatc ggatgacacc caccccgcaa cggaatcctg     240
gagttcaaag agggtgtcgt ctacggcatt taggtataga tggcataggg tttgacgtaa     300
gctgaaagct gattacgaga catgagacaa cgaaaataca acggttgtat gcgttcccgt     360
gcttactaaa gtgatatcca agagcaacac agccgaaaga aaccgatgct gtctgagggg     420
ttcctttaga gtctacatgg taacggtgca tgatagaaac atcaaatggc caatcaagtt     480 agtataccetg acgctacatc gctttcttcc ggatcttgcc taaatatat gtgcctgtcc     540 gaactgtcgg tactgcttcg tactaactgt tcttccgttg aagtcctagg acaagcgccg     600
cgtttgtaga cctacatgat gccacatctt aaagcaggga tctgagacat tttctaaggc     660
atccatatag gcattgggcg ctaagtcggc attgaaggag ataagggggg tgtgaaagtg     720
gtgtgtcaaa aggaggtcga ttggctatac cagccgctaa gcaggtgggc tagcagctgt     780
ctgcagctgt gaataacgtc acttgcttag gtatgtccac ctaatgtcag cagatgcaaa     840
```

```
tgctgattgg gttaaaatgg gcatgtagtg taggtgccga aaacacgttt agatctagtt      900
aaagggaagc tgaaagctga acctgtcaga aataagcctg ttggaataca acgttgataa      960
cccaattcag tcgtcaaggg tgtcctgata tgctggagct tccctgtcgc attgtggggt     1020
aactatttca tagtggggca gaatgcaact ctattttcaa ttgaatctaa actattctgg     1080
gtaggagttc tcaatggtct tctcgctgtc acttacacac atcatggggg tcaacaacgt     1140
atacagcttc atagagagtg cggcattgaa gtagctaccg catcgaaccc ggaagcggtt     1200
caagacatgg gcgtacgtag atacatagag tcatagaaac ataaaaggag cttgaagaac     1260
cattcaaatc ctaagggtct ctcttctttc tgcatcacat caagaatcat acactcaaac     1320
caggaactct ttctatcttc cctatagcaa ttcccaaaac ccatcaatca acctaaca      1378

<210> SEQ ID NO 2
<211> LENGTH: 1089
<212> TYPE: DNA
<213> ORGANISM: Mycelia sterilia

<400> SEQUENCE: 2
taaactccca tctatagcgg ttggctgaaa agggagagcg gcaggagaga tcagtctttt       60
gaccagcttg gagatctgat ctgtgtttca gtctcagtaa cttgtgtgga agttacactt      120
ctggtctccc tccttaccag ccctccaggc caaccacaag atgttaggag tttcgctcat      180
ttatatggct ctggcgatga gtagcattta tgaggcatgc acgacatggc tctactgctg      240
ctctgttggt taggttacct tagctagaca atatcacaat acaaaatgtg gtttccacat      300
gtcagctggt tctaccgtag tctgagtgaa atgggtaatt gatatattga gcttgacccc      360
gcaatattgt aacagagcca acaatgggtc acctggcccc ccagacatgt ggctatataa      420
gctacctgtc tagcaatcag acttactgat agaacgtccc cctatatgtc ataaaataag      480
tcactactag aactaccgac agtgtgaaat ccgacagtgt ctggtctgtt gaacatgtca      540
tgtctatatg aatgaataag aagaaggtgt gacgggttag tacgaatctg tatgataatc      600
aatggtagca gtgatggtaa acagcggatc gggatctagc actgctatgt ctgggtatgt      660
aatcctggct atgttcataa gggcgacata gaaagaatac ctcagtgtca gcatacgtaa      720
gctctgtaca tttcactgca aatttctgaa caattggaga gcattatgaa atactaaatg      780
gaactcctca ttataagtgg aaaacagagc gccctttttat tatgaaacag aagcgtcaag      840
aacgtctttc aacgtcatca gaggcgttcc atccagatca tactttccct tgaaccatgt      900
tctcgcattc agaatcgtag cgatggaaac cgtccagggt tgcctgtcat tcccttgcgt      960
cccttgcaat aaaatcgtat taccatttc tttcgcagcg ccggtcaacg tgagcgacgt     1020
gcccacgttg gagtccacaa tgaccagtgg atcgtcatcc acgccactca ctgcaatgag     1080
tcgcccggg                                                             1089

<210> SEQ ID NO 3
<211> LENGTH: 29
<212> TYPE: DNA
<213> ORGANISM: Artificial Sequence
<220> FEATURE:
<223> OTHER INFORMATION: Description of Artificial Sequence:primer for
      Abp1 gene

<400> SEQUENCE: 3
ggggaattcg tgggtggtga tatcatggc                                          29

<210> SEQ ID NO 4
```

-continued

```
<211> LENGTH: 24
<212> TYPE: DNA
<213> ORGANISM: Artificial Sequence
<220> FEATURE:
<223> OTHER INFORMATION: Description of Artificial Sequence:primer for
      Abp1 gene

<400> SEQUENCE: 4
gggggatcct tgatgggttt tggg                                              24

<210> SEQ ID NO 5
<211> LENGTH: 27
<212> TYPE: DNA
<213> ORGANISM: Artificial Sequence
<220> FEATURE:
<223> OTHER INFORMATION: Description of Artificial Sequence:primer for
      Abp1 gene

<400> SEQUENCE: 5
gggggatcct aaactcccat ctatagc                                           27

<210> SEQ ID NO 6
<211> LENGTH: 29
<212> TYPE: DNA
<213> ORGANISM: Artificial Sequence
<220> FEATURE:
<223> OTHER INFORMATION: Description of Artificial Sequence:primer for
      Abp1 gene

<400> SEQUENCE: 6
gggtctagac gactcattgc agtgagtgg                                         29

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence:primer for
      Abp1 gene

<400> SEQUENCE: 7
ctcaaaccag gaactctttc                                                   20

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence:primer for
      Abp1 gene

<400> SEQUENCE: 8
gacatgtgga aaccacattt tg                                                22
```